United States Patent [19]
Lee

[11] Patent Number: 5,836,018
[45] Date of Patent: Nov. 17, 1998

[54] DETACHABLE NECKTIE WITH MAGNETIC FIELD GENERATING MEANS

[76] Inventor: Ming Lee, No. 79, Wen Chou Street, Taipei City, Taiwan

[21] Appl. No.: 968,471

[22] Filed: Nov. 12, 1997

[51] Int. Cl.⁶ ............................. A41D 25/02; A61N 2/08
[52] U.S. Cl. ..................... 2/144; 2/155; 2/153; 600/15
[58] Field of Search ............................. 2/144, 145, 146, 2/148, 150, 152.1, 153, 155, 156; 600/9, 15

[56] References Cited

U.S. PATENT DOCUMENTS

| | | | |
|---|---|---|---|
| 178,611 | 6/1876 | Dye | 600/15 |
| 482,547 | 9/1892 | Cole | 2/155 |
| 1,431,268 | 10/1922 | Spiegler | 2/155 |
| 3,921,620 | 11/1975 | Nakayama | 600/15 |
| 4,095,587 | 6/1978 | Ishikawa | 600/15 |
| 4,173,792 | 11/1979 | Intengan | 2/144 |
| 4,587,956 | 5/1986 | Griffin et al. | 600/15 |
| 5,084,916 | 2/1992 | Austin | 2/153 |
| 5,088,120 | 2/1992 | Yen | 2/152 R |
| 5,109,547 | 5/1992 | Abdallah | 2/145 |
| 5,478,303 | 12/1995 | Foley-Nolan et al. | 600/15 |
| 5,493,731 | 2/1996 | Amnott | 2/148 |
| 5,720,046 | 2/1998 | Lopez et al. | 600/15 |

Primary Examiner—Amy B. Vanatta
Attorney, Agent, or Firm—Rosenberg, Klein & Bilker

[57] ABSTRACT

A necktie which includes a neckband adapted for putting over the user's neck, a plurality of magnetic elements fixedly mounted on the neckband at an inner side and equally spaced from one another and adapted to produce magnetic field for acting with the magnetic field of the body of the user, a coupling box coupled to the neckband, an apron unit, and a connector adapted to connect the apron unit to the coupling box.

10 Claims, 8 Drawing Sheets

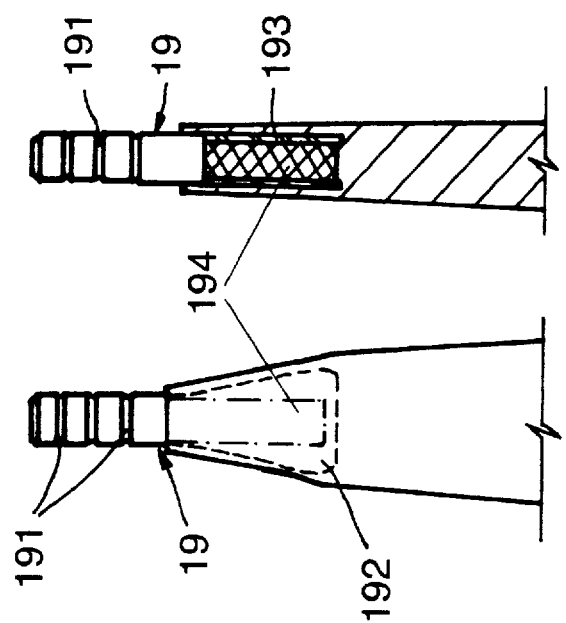

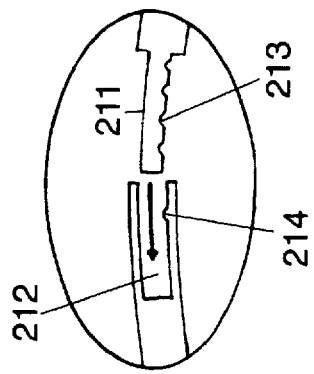
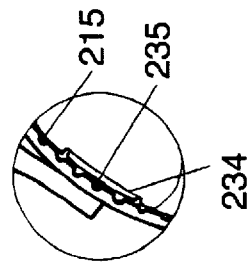
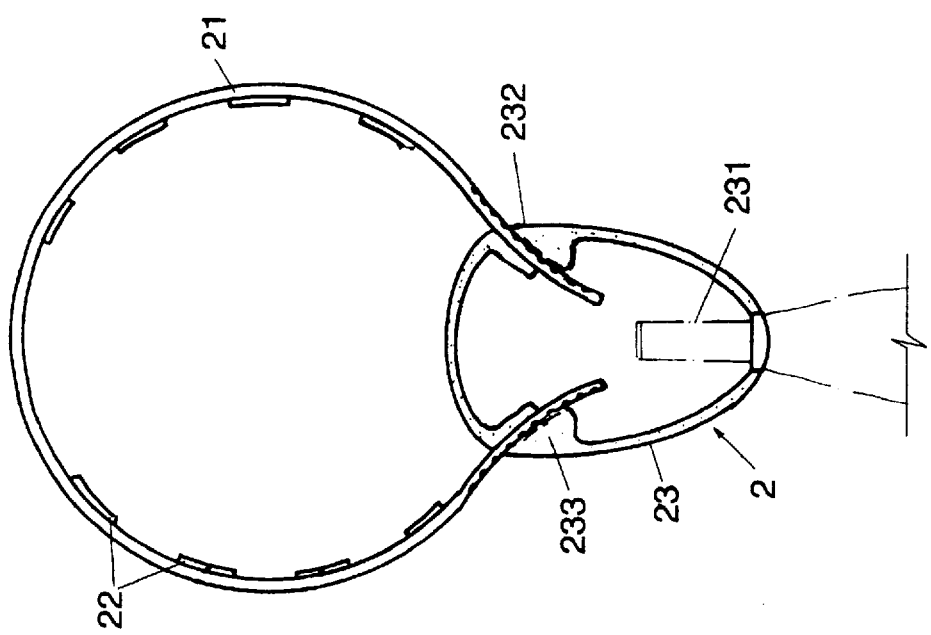

DETACHABLE NECKTIE WITH MAGNETIC FIELD GENERATING MEANS

BACKGROUND OF THE INVENTION

The present invention relates to neckties, and more particularly to such a necktie which is mounted with a plurality of magnetic elements that produce a magnetic field to act with the magnetic field from the user's body, so as to stimulate the circulation of blood. The necktie is made detachable so that the apron unit can be detached from the neckband for a replacement.

It is well known that employing a certain magnetic field to act with the magnetic field from a human body can stimulate the circulation of blood. A variety of magnetic field generating products such as magnetic beds, magnetic pillows, magnetic wrist chains, magnetic rings, etc., have been developed for this purpose. However, except magnetic wrist chains and magnetic rings, these magnetic field generating products cannot be constantly carried on the user. Further, regular neckties are commonly made in integrity, i.e., the apron unit (the front apron and rear apron) cannot be detached from the neck end for a replacement. Therefore, a necktie provides only one particular design.

SUMMARY OF THE INVENTION

The present invention has been accomplished under the circumstances in view. It is one object of the present invention to provide a necktie which produces a magnetic field around the user's neck to act with the magnetic field from the user's body, so as to stimulate the circulation of the user's blood. It is another object of the present invention to provide a necktie which has means to support the neck end of the necktie in shape. It is still another object of the present invention to provide a necktie which is detachable so that the apron unit can be detached from the neck end for a replacement. To achieve these and other objects of the present invention, there is provided a necktie which comprises a neckband adapted for putting over the user's neck, a plurality of magnetic elements fixedly mounted on the neckband at an inner side and equally spaced from one another and adapted to produce magnetic field for acting with the magnetic filed of the body of the user, a coupling box coupled to the neckband, an apron unit, and a connector adapted to connect the apron unit to the coupling box. According to another aspect of the present invention, the connector has a springy bottom flap fastened to the apron unit, which springy bottom flap can be deformed to support the neck end of the apron unit into shape.

BRIEF DESCRIPTION OF THE DRAWINGS

FIG. 3-1 is a side view in section of the coupling box of the necktie shown in FIG. 1.

FIG. 4-1 is a schematic drawing showing the action of the spring leaves and the resilient neckband elements of the neckband according to an alternate form of the first embodiment.

FIG. 5-1 is a perspective view of the connector according to the first embodiment of the present invention, showing the springy flap of the connector bilaterally bent forwards and backwards.

FIG. 5-2 shows an alternate form of the connector according to the first embodiment of the present invention.

FIG. 6-1 is an enlarged view of the apron unit shown in FIG. 6.

FIG. 7 is a sectional view of a necktie according to a second embodiment of the present invention.

FIG. 7-1 is an enlarged view of a part of FIG. 7, showing the top end structure of the resilient neckband elements of the neckband.

FIG. 7-2 is an enlarged view of a part of FIG. 7, showing the bottom end of one resilient neckband element of the neckband fastened to one retainer spring in one locating block.

FIG. 8-1 is an enlarged view of a part of FIG. 8, showing the steel ball forced sideways against the neckband.

DETAILED DESCRIPTION OF THE PREFERRED EMBODIMENT

Figure 1:
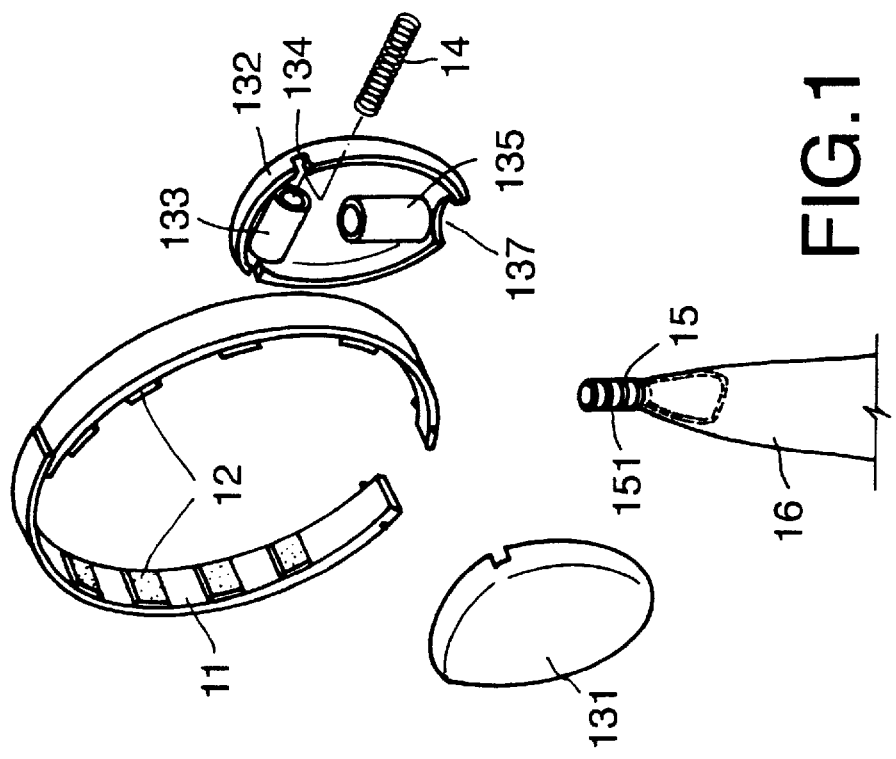
FIG. 1 is an exploded view of a necktie according to a first embodiment of the present invention.
Figure 2:
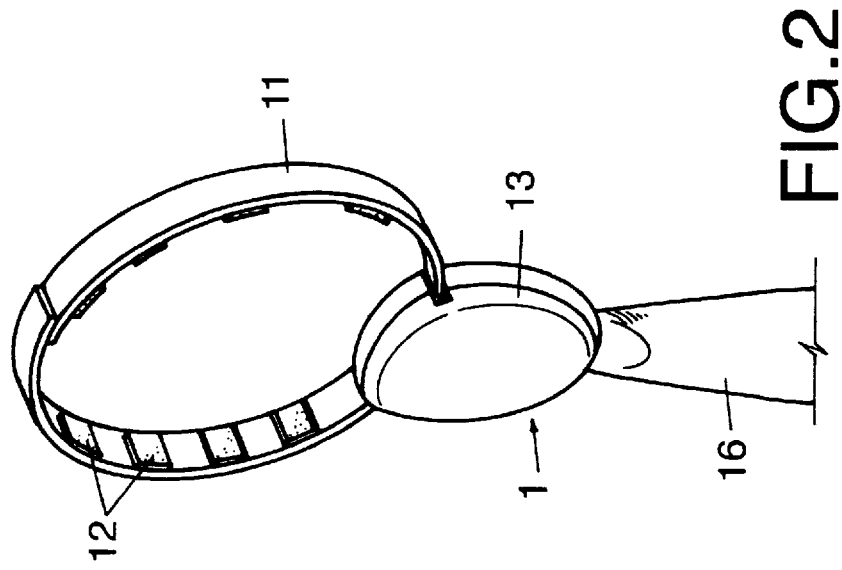
FIG. 2 is a perspective assembly view of the necktie shown in FIG. 1.

Referring to FIGS. 1 and 2, a necktie 1 in accordance with a first embodiment of the present invention is generally comprised of a neckband 11, a plurality of magnetic elements 12 fixedly mounted on the inner side of the neckband 11 and equally spaced from one another, a coupling box 13 joining the two opposite ends of the neckband 11, an apron unit 16, and a connector 15 connected between the coupling box 13 and the apron unit 16.

Figure 3:
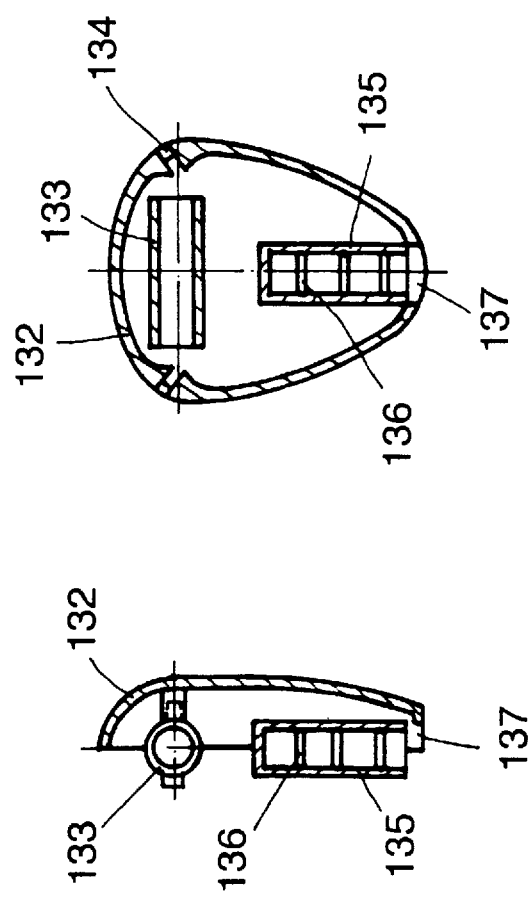
FIG. 3 is a front view in section of the coupling box of the necktie shown in FIG. 1.

Referring to FIGS. 3 and 3-1, and FIG. 1 again, the coupling box 13 comprises a casing 132, the casing 132 comprising a transverse barrel 133, a longitudinal barrel 135 which has a plurality of vertically spaced inside annular flanges 136 raised around its inside wall, two plug holes 134 pierced through the periphery at two opposite sides and bilaterally aligned with the transverse barrel 133, and a bottom insertion hole 137 aligned with the longitudinal barrel 135, a cover shell 131 covered on the casing 132, and a spring 14 mounted in the transverse barrel 133. The two opposite ends of the neckband 11 are respectively inserted through the plug holes 134 into the transverse barrel 133, and forced into engagement with the two opposite ends of the spring 14 (the two opposite ends of the neckband 11 are provided with raised portions for engaging into the two opposite ends of the spring 14).

Figures 1, 5:
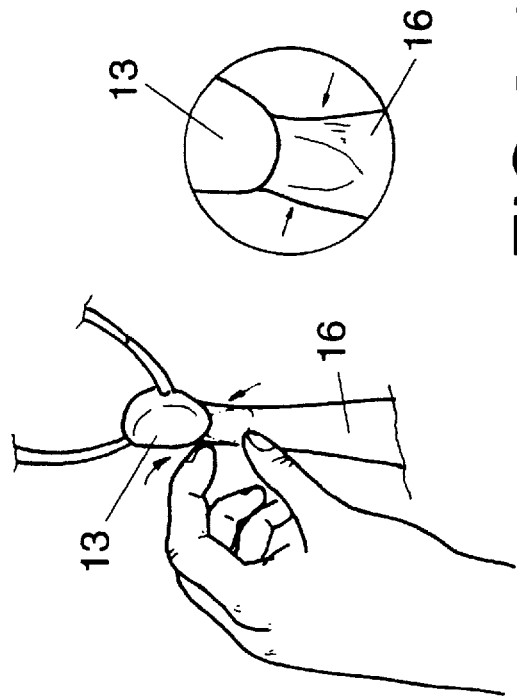
FIG. 5 is a schematic drawing showing the connector fastened to the apron unit according to the first embodiment of the present invention.

Referring to FIGS. 5 and 5-1, and FIG. 1 again, the connector 15 is a cylindrical member adapted for plugging into the longitudinal barrel 135 of the coupling box 13, having a plurality of vertically spaced outside annular grooves 151 adapted for coupling to the annular flanges 136 inside the longitudinal barrel 135, a flexible flap 152 extended from its bottom end, and a longitudinal rib 153 on the middle of the flexible flap 152. The flexible flap 152 can be bilaterally bent inwards and outwards to define a desired contained angle. When the connector 15 is inserted through the insertion hole 137 into the longitudinal barrel 135 of the casing 132 of the coupling box 13, the outside annular grooves 151 of the connector 15 are respectively forced into engagement with the inside annular flanges 136 of the connector 15, and therefore the connector 15 and the coupling box 13 are fastened together. The apron unit 16 is fixedly connected to the connector 15 and covered over the flexible flap 152. The shell of the apron unit 16 can decorated with any of a variety of designs.

Figures 1, 4:
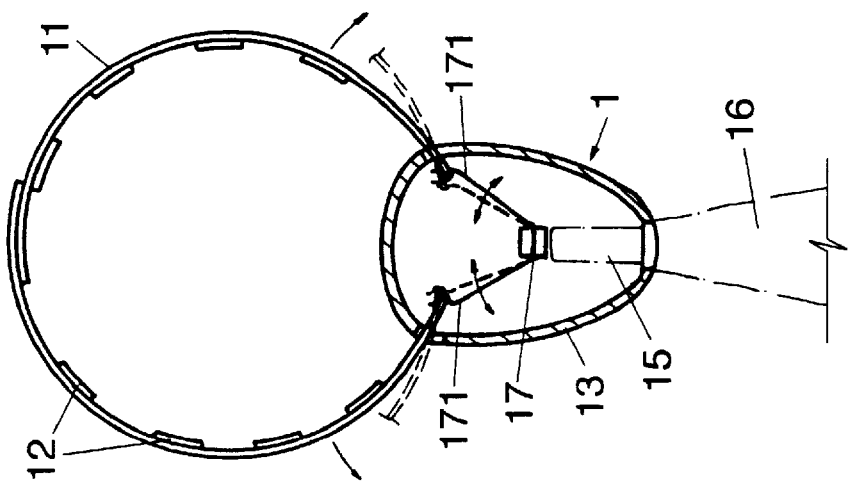
FIG. 4 is a schematic drawing showing the action of the spring and the resilient neckband elements of the neckband according to the first embodiment of the present invention.
Figure 4:
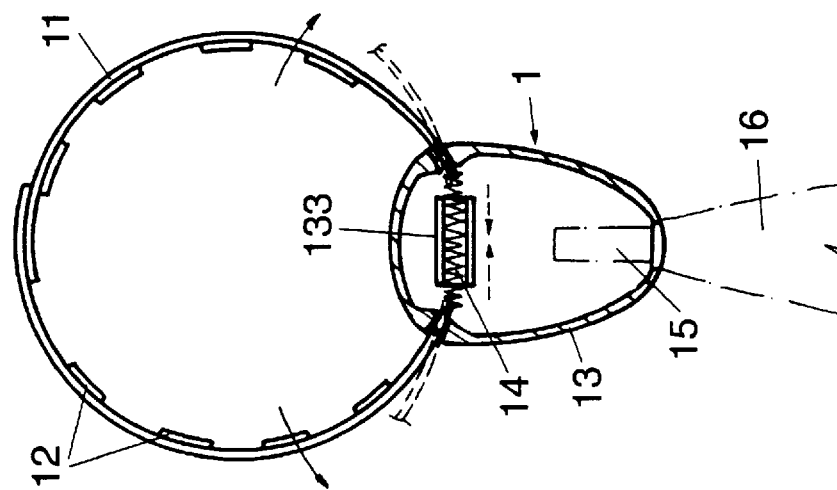
Figures 2, 4:
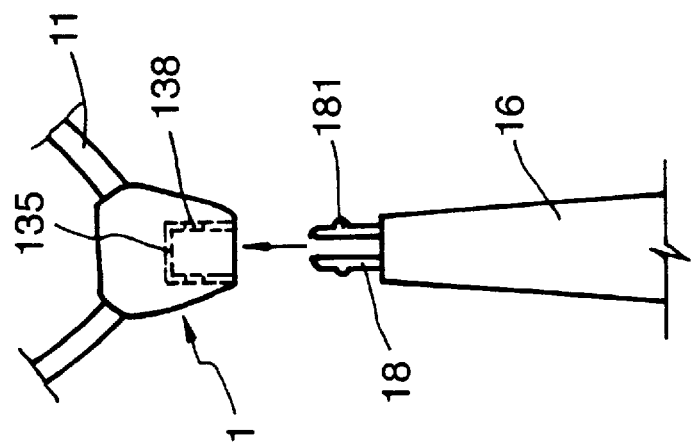
Figures 1, 6:
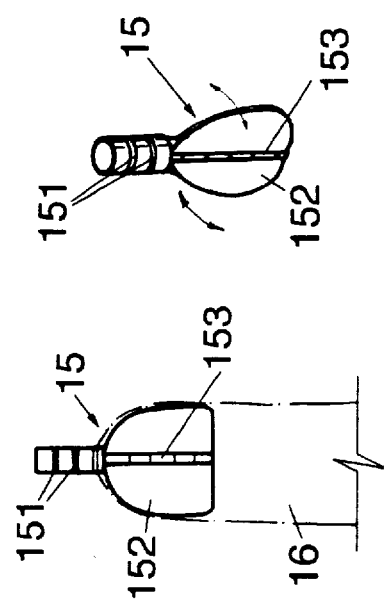
FIG. 6 is a schematic drawing showing the neck end of the apron unit squeezed against the springy flap of the connector and supported on the deformed springy flap into shape.

Referring to FIGS. 4 and 6, the neckband 11 is comprised of two smoothly arched resilient neckband elements respectively fastened to the coupling box 13. When the two resilient neckband elements of the neckband 11 are installed in the coupling box 13, the free ends of the resilient neckband elements are automatically attached to each other by means of their resilient material property, and therefore the neckband 11 and the coupling box 13 form a loop adapted for putting over the user's neck. By pulling the free ends of the resilient neckband elements of the neckband 11 apart, the neckband 11 can be conveniently fastened to the user's neck. When the free ends of the resilient neckband elements of the neckband 11 are pulled apart, the fixed ends of the resilient neckband elements of the neckband 11 are forced toward each other to compress the spring 14. After the neckband 11 has been put over the user's neck and released from the hands, the spring 14 imparts and outward pressure to the fixed ends of the resilient neckband elements of the neckband 11, and therefore the free ends of the resilient neckband elements of the neckband 11 are forced to attach to each other again. The user can then deform the flexible flap 152 of the connector 15 to set the top end of the apron unit 16 into the desired shape.

FIG. 4-1 shows an alternate form of the coupling box 13. According to this alternate form, the coupling box 13 comprises a spring holder 17 on the inside, and two spring leaves 171 bilaterally fastened to the spring holder 17. The spring leaves 171 have a respective bottom end fastened to the spring holder 17, and a respective top end adapted to hold the neckband 11. When the neckband 11 is opened, the spring leaves 171 are forced inwards toward each other; when the neckband 11 is released from the hands, the neckband 11 is immediately forced by the spring power of the spring leaves 171 back to the closed status.

FIG. 4-2 shows an alternate form of the connector 15. According to this alternate form, the connector 15 comprises two coupling rods 18 respectively inserted into the longitudinal barrel 135 of the coupling box 13. The coupling rods 18 have a respective hooked portion 181 respectively forced into engagement with a respective retaining hole 138 inside the longitudinal barrel 135.

FIG. 5-2 shows another alternate form of the connector according to the present invention. According to this alternate form, the connector, referenced by 19, comprises a plurality of vertically spaced outside annular grooves 191 adapted for coupling to the longitudinal barrel 135 of the aforesaid coupling box 13, and a springy support unit 192 extended from its bottom end and adapted for supporting the neck end 192 of the necktie in shape. The support unit 192 comprises two parallel springy leaves 193 downwardly extended from the bottom end of the connector 19, and an elongated spacer 194 longitudinally retained between the springy leaves 193. The elongated spacer 194 has a certain thickness so that the neck end 192 of the necktie can be supported in shape. When the user squeeze two opposite lateral sides of the springy support unit 192 with the fingers, the springy support unit 192 is deformed and turned to a substantially arched profile for supporting the neck end 192 of the necktie in shape.

FIGS. 7, 7-1 and 7-2 show a necktie according to a second embodiment of the present invention. According to this alternate form, the neck band 22 has a plurality of magnetic elements 22 arranged on its inner side; the two resilient neckband elements of the neckband 21 of the necktie 2 have a respective top end respectively terminated in a plug strip 211 with longitudinally spaced locating grooves 213 and a longitudinal plug hole 212 with a retainer flange 214, and a respective bottom end respectively made with a plurality of longitudinally spaced coupling grooves 215. When the plug strip 211 is inserted into the plug hole 212, the retainer flange 214 is forced into engagement with one locating groove 213, and therefore the neckband 21 is closed. By shifting the engagement point between the retainer flange 214 and the locating grooves 213, the diameter of the neckband 21 is adjusted. The coupling box 23 comprises a longitudinal barrel 231 for mounting the apron unit, two plug holes 232 at two opposite sides for receiving the bottom ends of the resilient neckband elements of the neckband 21, two hollow locating blocks 233 respectively raised from the inside and connected to the plug holes 232, the locating blocks 233 having a respective recessed portion 234 on the inside, and a respective retainer spring 235 mounted in the respective recessed portion 234 and adapted for securing the bottom ends of the resilient neckband elements of the neckband 21 in place. The retainer springs 235 inside the locating blocks 233 have raised portions adapted to engage into the locating grooves 215 on the bottom ends of the resilient neckband elements of the neckband 21.

Figures 1, 8:
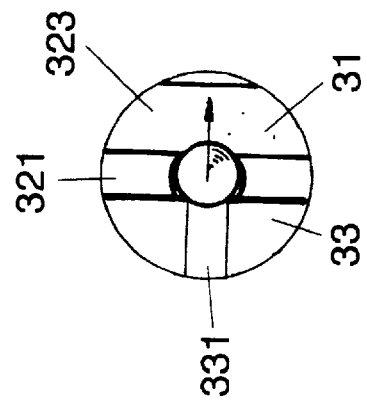
FIG. 8 is a sectional view of a necktie according to a third embodiment of the present invention.
Figure 8:
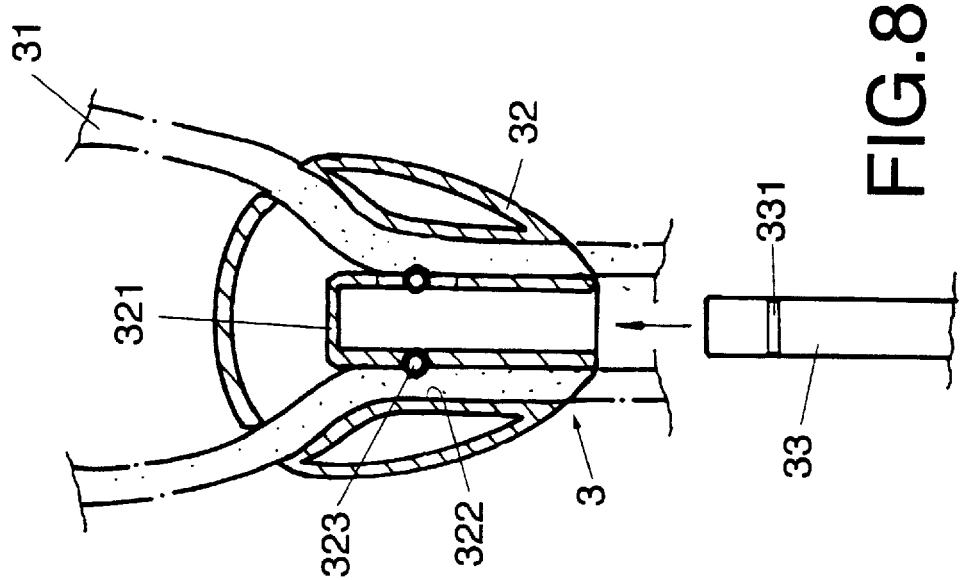

FIGS. 8 and 8-1 show a necktie according to a third embodiment of the present invention. According to this embodiment, the neckband 31 is a soft cord having two opposite ends respectively inserted into two mounting holes 322 in the coupling box 32 at two opposite sides of the longitudinal barrel 321. The coupling box 32 comprises two steel balls 323 revolvably supported in a respective hole at two opposite sides of the longitudinal barrel 321. The connector 33 which is adapted to secure the apron unit of the necktie 3 to the coupling box 32 has an annular groove 331 around the periphery. When the connector 33 is plugged into the longitudinal barrel 321, the steel balls 323 are respectively supported in the annular groove 331 of the connector 33 and forced by the connector 33 to retain the neckband 31 in place. When the connector 33 is disconnected from the longitudinal barrel 321, the steel balls 323 can be freely turned in the respective holes on the longitudinal barrel 321, and therefore the two opposite ends of the neckband 31 can be moved in the mounting holes 322 to adjust the neckband 31 subject to the diameter of the user's neck.

It is to be understood that the drawings are designed for purposes of illustration only, and are not intended as a definition of the limits and scope of the invention disclosed.

What the invention claimed is:

1. A necktie comprising:
   a neckband adapted for putting over the user's neck,
   a plurality of magnetic elements fixedly mounted on said neckband at an inner side and equally spaced from one another;
   a coupling box coupled to said neckband;
   an apron unit; and
   a connector adapted to connect said apron unit to said coupling box.

2. The necktie of claim 1, wherein said neckband is comprised of two arched resilient neckband elements, said resilient neckband elements having a respective fixed end respectively connected to said coupling box, and a respective free end attached to each other for permitting said neckband to be opened for putting over the user's neck by removing the free ends of said resilient neckband elements from each other.

3. The necktie of claim 2, wherein said coupling box comprises a longitudinal barrel aligned with a bottom insertion hole thereof and adapted for holding said connector, a transverse barrel aligned between two opposite side plug holes thereof and adapted for holding the fixed ends of said resilient neckband elements of said neckband, and a spring mounted inside said transverse barrel and connected between the fixed ends of said resilient neckband elements of said neckband.

4. The necktie of claim 2, wherein said coupling box comprises a longitudinal barrel aligned with a bottom insertion hole thereof and adapted for holding said connector, a spring holder spaced above said longitudinal barrel, and two spring leaves having a respective bottom end fixedly fastened to said spring holder and a respective top end respectively connected to the fixed ends of said resilient neckband elements of said neckband.

5. The necktie of claim 3, wherein said longitudinal barrel has a plurality of inside annular flanges vertically spaced on the inside; said connector is inserted through the bottom insertion hole of said coupling box and plugged into said longitudinal barrel, said connector having a plurality of outside annular grooves vertically spaced around the periphery and forced into engagement with the inside annular flanges of said longitudinal barrel.

6. The necktie of claim 3, wherein said longitudinal barrel of said coupling box has two retaining holes on the inside; said connector comprises two coupling rods respectively inserted into said longitudinal barrel of said coupling box, said coupling rods having a respective hooked portion respectively forced into engagement with the retaining holes inside said longitudinal barrel.

7. The necktie of claim 1, wherein said connector has a springy bottom flap fastened to said apron unit and adapted for supporting a neck end of said apron unit into shape, said springy bottom flap having a longitudinal rib on the middle.

8. The necktie of claim 1, wherein said connector comprises a support unit extended from a bottom end thereof and fastened to a neck end at one end of said apron unit and adapted to support said neck end in shape, said support unit comprising two parallel springy leaves, and an elongated spacer longitudinally retained between said springy leaves.

9. The necktie of claim 1, wherein said neckband comprises two resilient neckband elements, said resilient neckband elements having a respective top end respectively terminated in a plug strip and a plug hole for connection to each other, and a respective bottom end respectively made with a plurality of longitudinally spaced coupling grooves for fastening to said coupling box, said plug strip having a plurality of longitudinally spaced locating grooves and being plugged into said plug hole, said plug hole having a retainer flange adapted to engage into one of said longitudinally spaced locating grooves; said coupling box comprises a longitudinal barrel adapted to receive said connector, two plug holes at two opposite sides adapted to receive the bottom ends of said resilient neckband elements of said neckband, two hollow locating blocks respectively raised from the inside and connected to said plug holes, said locating blocks having a respective recessed portion on the inside, and two retainer springs respectively mounted in the recessed portion of each locating block and adapted for securing the bottom ends of said resilient neckband elements of said neckband in place, said retainer springs having raised portions adapted to engage into the locating grooves on the bottom ends of said resilient neckband elements of said neckband.

10. The necktie of claim 1, wherein said coupling box comprises a longitudinal barrel adapted to receive said connector, two elongated mounting holes spaced by said longitudinal barrel, two transverse holes pierced through two opposite side walls of said longitudinal barrel and respectively disposed in communication with said mounting holes, and two steel balls revolvably supported in said transverse holes; said neckband is a soft cord having two opposite ends respectively inserted into the two mounting holes of said coupling box, the two opposite ends of said neckband being secured in said mounting holes of said coupling box by said steel balls when said connector is plugged into the longitudinal barrel of said coupling box; said connector has one end plugged into said longitudinal barrel of said coupling box to force said steel balls bilaterally outwards, causing said steel balls to partially project into said mounting holes in securing the two opposite ends of said neckband in said mounting holes.

* * * * *